United States Patent [19]

Takeda et al.

[11] Patent Number: 4,567,175

[45] Date of Patent: Jan. 28, 1986

[54] 8-CHLORO-1,5-BENZOTHIAZEPINE DERIVATIVES

[75] Inventors: Mikio Takeda, Urawa; Tokuro Oh-ishi, Tokyo; Hiromichi Nakajima, Urawa; Taku Nagao, Tokyo, all of Japan

[73] Assignee: Tanabe Seiyaku Co., Ltd., Japan

[21] Appl. No.: 610,856

[22] Filed: May 16, 1984

[30] Foreign Application Priority Data

Jun. 3, 1983 [GB] United Kingdom ................ 8315364
Jan. 14, 1984 [GB] United Kingdom ................ 8400983

[51] Int. Cl.$^4$ ................ C07D 281/10; A61K 31/55
[52] U.S. Cl. ........................ 514/211; 260/239.3 B
[58] Field of Search ............... 260/239.3 B; 424/275; 514/211

[56] References Cited

U.S. PATENT DOCUMENTS 3,562,257  2/1971  Kugita et al. ................ 260/239.3 B

FOREIGN PATENT DOCUMENTS 1240982  7/1971  United Kingdom ......... 260/239.3 B

Primary Examiner—Robert T. Bond

Attorney, Agent, or Firm—Scully, Scott, Murphy & Presser

[57] ABSTRACT

Novel 8-chloro-1,5-benzothiazepine derivatives of the formula:

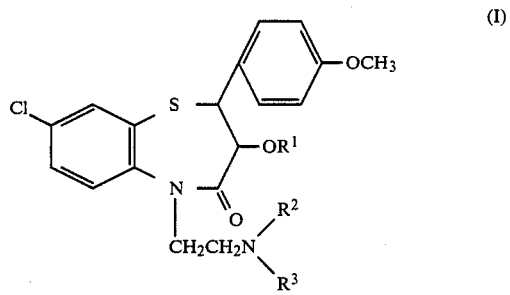

wherein $R^1$ is hydrogen, lower alkyl or a group of the formula: $R^4CO-$, each of $R^2$ and $R^3$ is lower alkyl and $R^4$ is hydrogen or lower alkyl, and a pharmaceutically acceptable acid addition salt thereof are disclosed. Said derivative (I) and a pharmaceutically acceptable acid addition salt thereof are useful as hypotensive agents and/or coronary or cerebral vasodilators.

20 Claims, No Drawings

8-CHLORO-1,5-BENZOTHIAZEPINE DERIVATIVES

This invention relates to novel 8-chloro-1,5-benzothiazepine derivatives and processes for preparing the same. More particularly, it relates to a compound of the formula:

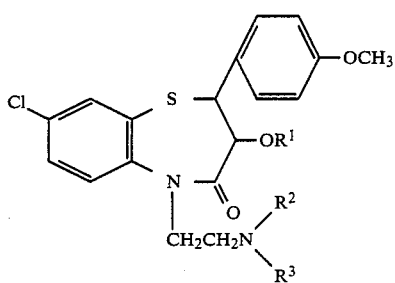

wherein $R^1$ is hydrogen, lower alkyl or a group of the formula: $R^4CO$—; each of $R^2$ and $R^3$ is lower alkyl and $R^4$ is hydrogen or lower alkyl, or a pharmaceutically acceptable acid addition salt thereof.

U.S. Pat. No. 3,562,257 discloses various benzothiazepine derivatives including 7-chloro-1,5-benzothiazepine derivatives such as 2-(4-methoxyphenyl)-3-hydroxy (or acetoxy)-5-[2-(dimethylamino)ethyl]-7-chloro-2,3-dihydro-1,5-benzothiazepin-4(5H)-one. Said U.S. Patent also discloses that these benzothiazepine derivatives shown antidepressive, tranquilizing and/or coronary vasodilating activities.

As a result of various investigations, we have now found that the compound (I) of the present invention or a pharmaceutically acceptable acid addition salt thereof is useful as a hypotensive agent and/or a cerebral or coronary vasodilator. The compound (I) of the invention is especially characteristic in that it shows a strong hypotensive activity. For example, when administered orally to spontaneously hypertensive rats (SHR), (+)-cis-2(4-methoxyphenyl)-3-acetoxy-5-[2-(dimethylamino)ethyl]-8-chloro-2,3-dihydro-1,5-benzothiazepin-4(5H)-one maleate at a dose of 30 mg/kg shows a decrease of about 86 mm Hg or 68 mm Hg in blood pressure of said SHR one or 4 hours after administration of the test compound.

The compound (I) of the present invention also shows a potent cerebral or coronary vasodilating activity. For example, (+)-cis-2-(4-methoxyphenyl)-3-acetoxy-5-[2-(dimethylamino)ethyl]-8-chloro-2,3-dihydro-1,5-benzothiazepin-4(5H)-one hydrochloride and (+)-cis-2-(4-methoxyphenyl)-3-propionyloxy-5-[2-(dimethylamino)ethyl]-8-chloro-2,3-dihydro-1,5-benzothiazepin-4(5H)-one oxalate when administered intraarterially to anesthetized dogs show remarkable increase in vertebral artery blood flow, and said cerebral vasodilating activity of the compounds of the invention are about 24 to 25 times stronger than that of papaverine and are about 5 times stronger than that of (+)-cis-2-(4-methoxyphenyl)-3-acetoxy-5-[2-(dimethylamino)ethyl]-7-chloro-2,3-dihydro-1,5-benzothiazepin-4(5H)-one hydrochloride. On the other hand, when the coronary vasodilating activity is estimated by the Langendorff method using isolated hearts of guinea pigs, said activity of (+)-cis-2-(4-methoxyphenyl)-3-acetoxy-5-[2-(dimethylamino)ethyl]-8-chloro-2,3-dihydro-1,5-benzothiazepin-4(5H)-one hydrochloride is about 10 times stronger than that of papaverine.

Moreover, the compound (I) of the present invention is characterized by its longer-lasting therapeutic effects (i.e., longer-lasting hypotensive activity and longer-lasting cerebral or coronary vasodilating activity) as compared with (±)-cis-2-(4-methoxyphenyl)-3-acetoxy-5-[2-(dimethylamino)-ethyl]-7-chloro-2,3-dihydro-1,5-benzothiazepin-4(5H)-one.

In addition, the compound (I) of the present invention has a potent platelet aggregation-inhibiting activity, shows no substantial side effects (e.g., central nervous system effect) and, at the same time, is low in toxicity. For example, the acute toxicity ($LD_{50}$) of (+)-cis-2-(4-methoxyphenyl)-3-acetoxy-5-[2-(dimethylamino)ethyl]-8-chloro-2,3-dihydro-1,5-benzothiazepin-4(5H)-one hydrochloride when orally administered to mice is more than 1000 mg/kg.

Representative examples of the compounds of the present invention include those of the formula (I) in which $R^1$ is hydrogen, lower alkyl of one to 5 carbon atoms such as methyl, ethyl, propyl, butyl or pentyl or a group of the formula: $R^4CO$— (wherein $R^4$ is hydrogen or lower alkyl of one to 5 carbon atoms such as methyl, ethyl, propyl, butyl or pentyl); and each of $R^2$ and $R^3$ is lower alkyl of one to 5 carbon atoms such as methyl, ethyl, propyl, butyl or pentyl. Among the compounds of the present invention, a preferred subgenus is those of the formula (I) in which $R^1$ is hydrogen, methyl, formyl, acetyl, propionyl, butyryl or valeryl, and each of $R^2$ and $R^3$ is alkyl of one to 3 carbon atoms. More preferred subgenus is those of the formula (I) in which $R^1$ is hydrogen, methyl, formyl, acetyl or propionyl, and each of $R^2$ and $R^3$ is methyl or ethyl. Another preferred subgenus is those of the formula (I) in which $R^1$ is hydrogen. Other preferred subgenus is those of the formula (I) in which $R^1$ is a group of the formula: $R^4CO$— (wherein $R^4$ is hydrogen or lower alkyl). Still other preferred subgenus is those of the formula (I) in which $R^1$ is acetyl or propionyl, $R^2$ is methyl and $R^3$ is methyl or ethyl. Further preferred subgenus is those of the formula (I) in which $R^1$ is acetyl or propionyl and $R^2$ and $R^3$ are methyl. Most preferred subgenus is those of the formula (I) in which $R^1$ is acetyl, $R^2$ is methyl and $R^3$ is methyl or ethyl.

While the compound (I) of the present invention can exist in the form of two stereoisomers (i.e., cis and trans isomers) or four optical isomers (i.e., (+)-cis, (−)-cis, (+)-trans and (−)-trans isomers) due to the two asymmetric carbon atoms involved therein, all of these optical isomers or a mixture thereof are included within the scope of the invention. Among said isomers, however, the cis isomer, especially the (+)-cis isomer, of the compound (I) is preferred for medicinal use.

According to the present invention, the compound (I) in which $R^1$ is hydrogen or a group of the formula: $R^4CO$— (wherein $R^4$ is the same as defined above) can be prepared by condensing a compound of the formula:

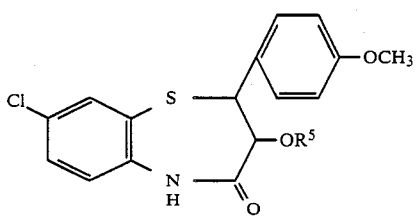 (II)

wherein R⁵ is hydrogen or a group of the formula: R⁴CO— (wherein R⁴ is the same as defined above), or a salt thereof with a compound of the formula:

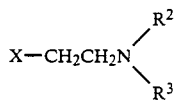 (III)

wherein $R^2$ and $R^3$ are the same as defined above and X is halogen, or a salt thereof to give a compound of the formula:

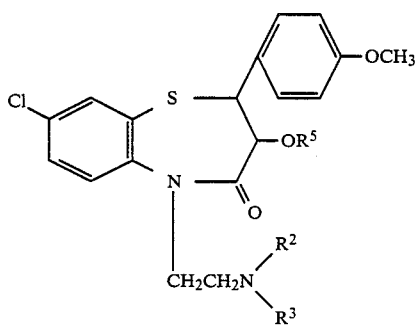 (I-a)

wherein $R^2$, $R^3$ and $R^5$ are the same as defined above.

Alternatively, the compound (I) in which $R^1$ is a group of the formula: R⁴CO— (wherein R⁴ is the same as defined above) can be prepared by condensing a compound of the formula:

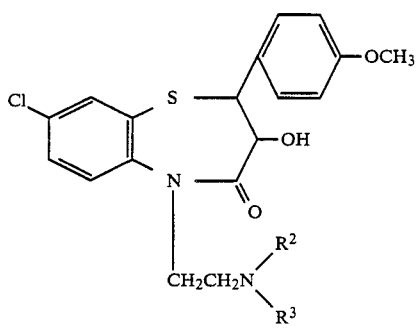 (I-b)

wherein $R^2$ and $R^3$ are the same as defined above, or a salt thereof with a compound of the formula:

R⁴COOH     (IV)

wherein R⁴ is the same as defined above, or a reactive derivative thereof to give a compound of the formula:

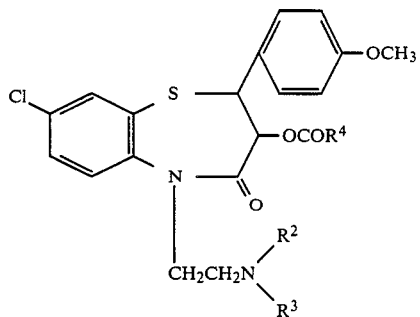 (I-c)

wherein $R^2$, $R^3$ and $R^4$ are the same as defined above.

On the other hand, the compound (I) in which $R^1$ is lower alkyl can be prepared by reacting the compound (I-b) or a salt thereof with a compound of the formula:

R⁶-X'     (V)

wherein R⁶ is lower alkyl and X' is a reactive residue, to give a compound of the formula:

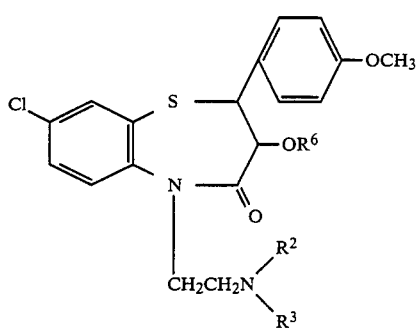 (I-d)

wherein $R^2$, $R^3$ and $R^6$ are the same as defined above.

The condensation of the compound (II) or a salt thereof with the compound (III) or a salt thereof can be carried out in a solvent. Suitable salt of the compound (II) includes, for example, alkali metal salts such as sodium or potassium salts. When the compound (II) is used in free form, it is preferred to carry out the reaction in the presence of an alkali agent. The alkali agent includes, for example, alkali metal hydroxide (e.g. potassium hydroxide, sodium hydroxide), alkali metal carbonate (e.g., potassium carbonate, sodium carbonate) and alkali metal hydride (e.g., sodium hydride). Examples of the salt of the compound (III) includes acid addition salts thereof such as hydrochloride, hydrobromide and so forth. Acetone, ethyl acetate, dimethylsulfoxide, dimethylformamide, acetonitrile, tetrahydrofuran and dioxane are suitable as the solvent. It is preferred to carry out the reaction at a temperature of 0° to 100° C., especially at 20° to 70° C.

The condensation of the compound (I-b) or salt thereof with a reactive derivative of the compound (IV) can be conducted in a solvent in the presence or absence of an acid acceptor. Examples of the salt of the compound (I-b) include acid addition salts thereof such as hydrochloride, hydrobromide and so forth. The reactive derivative of the compound (IV) includes, for example, mixed acid anhydride (e.g., acid anhydride of formic acid and acetic acid), lower alkanoic acid anhydride (e.g., acetic anhydride, propionic anhydride) and lower alkanoyl halide (e.g., acetyl chloride, propionyl chloride, butyryl chloride, valeryl chloride). The acid acceptor includes, for example, pyridine, triethylamine, N-methylpiperidine, N-methylmorpholine, N-methylpyrrolidine and N-ethyl-N,N-diisopropylamine. Acetic acid, chloroform, dichloromethane, dimethylformamide and tetrahydrofuran are suitable as the solvent. When an excess amount of acetic anhydride is used as the reactive derivative of the compound (IV), it is not always necessary to use the solvent because said acetic anhydride serves as the solvent. It is preferred to carry out the reaction at a temperature of −10° to 140° C., i.e., at a temperature of 20° to 140° C. if the lower alkanoic acid anhydride is used as the reactive derivative of the compound (IV); or at a temperature of −10° to 100° C. if the mixed acid anhydride or the lower alkanoic acid halide is used as the reactive derivative.

On the other hand, when the compound (IV) is used in the form of free acid, the condensation thereof with the compound (I-b) or a salt thereof may be carried out in a solvent in the presence of a condensing agent. The condensing agent includes, for example, dicyclohexylcarbodiimide, N,N'-carbonyldiimidazol, 1-methyl-2-halopyridinium iodide (e.g., 1-methyl-2-bromopyridinium iodide), methoxyacetylene and $(C_6H_5)_3P-CCl_4$. Methylene chloride, 1,2-dichloroethane, chloroform, benzene, toluene, tetrahydrofuran and dioxane are suitable as the solvent. It is preferred to carry out the reaction at a temperature of 0° to 50° C., especially at 0° to 25° C.

The reaction of the compound (I-b) or a salt thereof with the compound (V) can be conducted in a solvent in the presence of an acid acceptor. Examples of the compound (V) include di-lower alkyl sulfate (e.g., dimethyl sulfate) and lower alkyl halide (e.g., methyl iodide, ethyl iodide). The acid acceptor includes, for example, sodium hydride, sodium hydroxide, potassium hydroxide, potassium carbonate and sodium carbonate. Benzene, toluene, tetrahydrofuran, dioxane, dimethylformamide, dimethylsulfoxide and the like are suitable as the solvent. It is preferred to carry out the reaction at a temperature of 20° to 100° C., especially at 20° to 60° C.

The starting compound (II) or (I-b) of the present invention involves four optical isomers (i.e., (+)-cis, (−)-cis, (+)-trans and (−)-trans isomers) due to the two asymmetric carbon atoms at the 2- and 3-positions of benzothiazepine skeleton. However, since all of the above-mentioned reactions of the invention can be carried out without racemization, the compound (I) of the invention in an optically active form can be readily obtained by the use of the corresponding optically active isomer of the compound (II) or (I-b) as the starting material.

The starting compound (II) in which $R^1$ is hydrogen is novel and can be prepared according to the methods shown by the following reaction scheme:

(Method A)

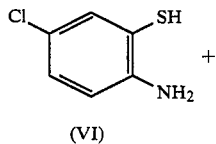
(VI)

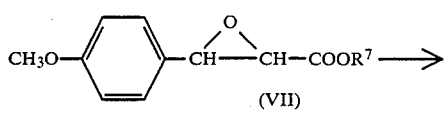
(VII)

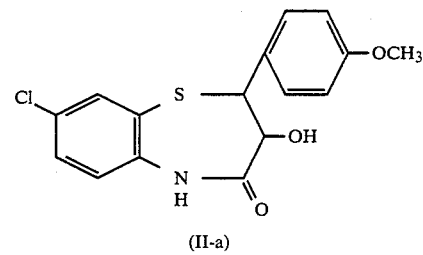
(II-a)

(Method B)

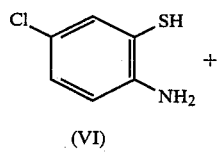
(VI)

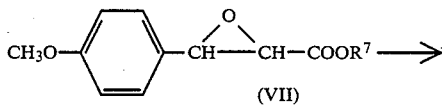
(VII)

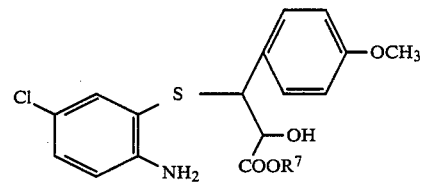
(VIII)

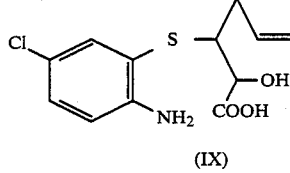
(IX)

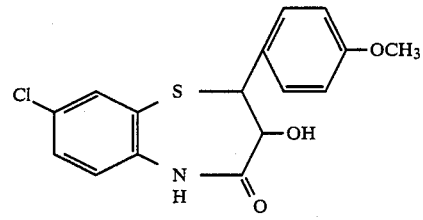
(II-a)

(Method C)

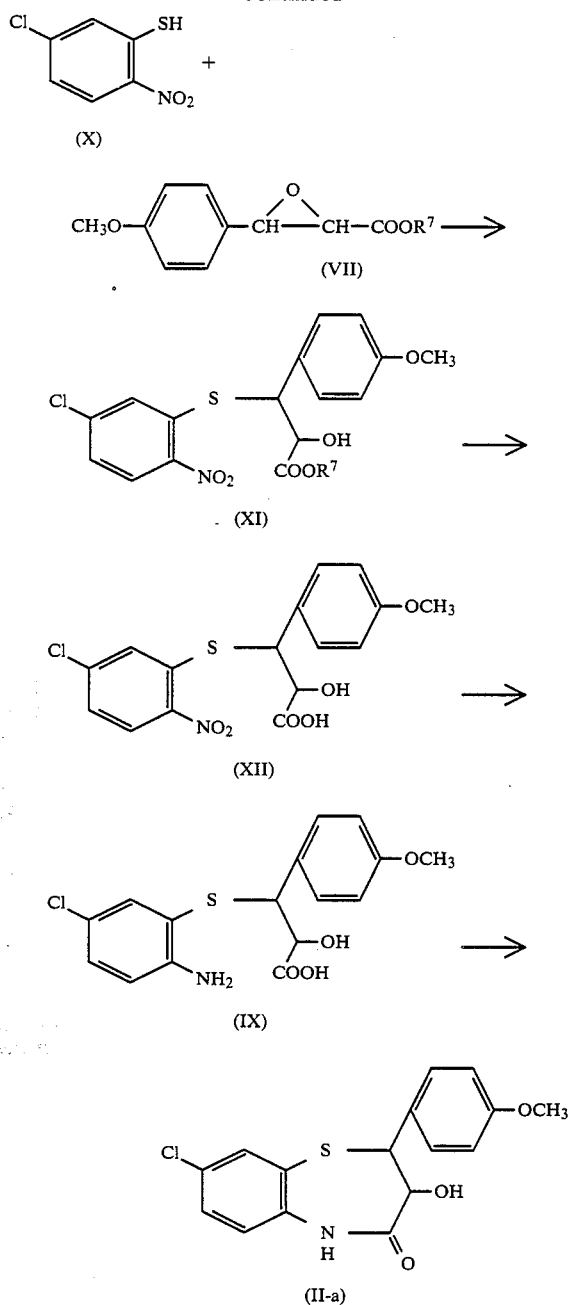

wherein R[7] is lower alkyl.

According to Method A, the compound (II-a) can be prepared by reacting 2-amino-5-chlorothiophenol (VI) with the 3-(p-methoxyphenyl)glycidate (VII).

On the other hand, according to Method B, the compound (II-a) can be prepared by (i) reacting 2-amino-5-chlorothiophenol (VI) with the 3-(p-methoxyphenyl)-glycidate (VII) to give the propionate compound (VIII), (ii) optionally hydrolyzing the compound (VIII) to give the propionic acid compound (IX) and (iii) subjecting the compound (VIII) or (IX) to intramolecular cyclization.

Further, according to Method (C), the compound (II-a) can be prepared by (i) reacting 2-nitro-5-chloro-thiophenol (X) with the 3-(p-methoxyphenyl)glycidate (VII) to give the propionate compound (XI), (ii) hydrolyzing the compound (XI) to give the compound (XII), (iii) reducing the compound (XII) to give the compound (IX) and (iv) subjecting the compound (IX) to intramolecular cyclization.

The reaction in Method A, i.e., the reaction of the compound (VI) with the compound (VII), can be accomplished by heating a mixture of the compound (VI) and the compound (VII) at a temperature of 150° to 160° C. The reaction may be carried out either in a solvent (e.g., xylene, diphenyl ether, p-cymene) or without solvent. When the compound (II-a) is formed in the form of a mixture of two stereoisomers (i.e., cis and trans isomers), they can be separated from each other by their difference in solubility in a solvent such as lower alkanol (e.g., ethanol) or by column chromatography.

The first step in Method B, i.e., the reaction of the compound (VI) with the compound (VII), can be accomplished by heating a mixture of the compounds (VI) and (VII) at a temperature of 40° to 110° C., especially at 60° to 100° C., in a solvent. Toluene, benzene, acetonitrile and dioxane are suitable as the solvent. When the starting compound (VII) is lower alkyl trans-3-(4-methoxyphenyl)glycidate, the threo isomer of the compound (VIII) is obtained.

The subsequent optional hydrolysis of the compound (VIII) can be conducted by treating said compound with an alkali agent in a solvent. The alkali agent includes, for example, potassium hydroxide, sodium hydroxide, potassium carbonate and sodium carbonate. Alkanol (e.g., methanol, ethanol) and a mixture of water and said alkanol are suitable as the solvent. It is preferred to carry out the reaction at a temperature of 0° to 100° C., especially at 25° to 100° C.

If required, the compound (IX) thus obtained may be optically resolved into each optically active enantiomers by using an optically active resolving agent such as optically active isomer of p-hydroxyphenylglycine ester or cinchonidine. For example, the optical resolution of (+)-threo-2-hydroxy-3-(2-amino-5-chloro-phenylthio)-3-(4-methoxyphenyl)propionic acid can be accomplished by the steps of reacting said compound with an optically active p-hydroxyphenylglycine methyl ester to form the diastereoisomeric salts thereof, and separating the diastereoisomeric salts from each other by selective crystallization. By said selective crystallization, less soluble diastereoisomeric salt is obtained as crystals from the solution, and the more soluble one remains dissolved in the solution. To illustrate more specifically, (+)-threo-2-hydroxy-3-(2-amino-5-chloro-phenylthio)-3-(4-methoxyphenyl)propionic acid forms the less soluble diastereoisomeric salt if L-p-hydroxy-phenylglycine methyl ester is used as the resolving agent, and, on the other hand, (−)-threo-2-hydroxy-3-(2-amino-5-chlorophenylthio)-3-(4-methoxyphenyl)-propionic acid forms the less soluble diastereoisomeric salt if D-p-hydroxyphenylglycine methyl ester is used as the resolving agent. Selective crystallization is carried out by recrystallizing the diastereoisomeric salts from a solvent such as lower alkanol (e.g., methanol, ethanol). After the optical resolution, the optically active compound (IX) in free form can be regenerated by treating the thus-obtained diastereoisomeric salt with an acid (e.g., hydrochloric acid).

The intramolecular cyclization of the thus-obtained racemic or optically active compound (VIII) or (IX) can be carried out by heating it either in a solvent or without solvent. Xylene, toluene, diphenyl ether, p- cymene and acetic acid are suitable as the solvent. It is preferred to carry out the reaction at a temperature of 110° to 160° C., especially under refluxing. Alternatively, the intramolecular cyclization of the compound (VIII) may be carried out at 0° to 50° C. in the presence of methylsulfinylcarbanion ($CH_3SOCH_2^-$) (prepared from dimethylsulfoxide and sodium hydride) in dimethylsulfoxide. Moreover, the intramolecular cyclization of the compound (IX) may also be carried out in a solvent in the presence of a condensing agent. Dicyclohexylcarbodiimide is used alone as the condensing agent or in combination with 1-hydroxybenzotriazole, 4-dimethylaminopyridine, N-hydroxyphthalimide, N-hydroxysuccinimide, trichlorophenol, p-nitrophenol or 3-hydroxy-4-oxo-3,4-dihydro-1,2,3-benzotriazine. Carbonyldiimidazole, ethoxyacetylene and 1-methyl-2-halopyridinium halide (e.g., 1-methyl-2-chloropyridinium iodide, 1-methyl-2-bromopyridinium iodide) are also used as the condensing agent. 1-Methyl-2-halopyridinium halide, the condensing agent, may be used in combination with a base such as triethylamine or tributylamine. Chloroform, dimethylformamide, carbon tetrachloride, dichloromethane, 1,2-dichloroethane, ethyl acetate, tetrahydrofuran and dioxane are suitable as the solvent. It is preferred to carry out the reaction at a temperature of −10° to 70° C.

The first step in Method C, i.e., the reaction of the compound (X) with the compound (VII), can be conducted in the presence or absence of a catalyst in a solvent. The catalyst includes, for example, Lewis acids such as zinc acetate, zinc iodide, zinc chloride, stannous chloride, stannous octylate, stannic chloride, stannic octylate, stannous stearate, boron trifluoride, sulfuric acid and perchloric acid. Other Lewis acids which are described in European patent publication No. 0 059 335 may also be used as the catalyst. Toluene, benzene, xylene, dioxane, tetrahydrofuran, acetonitrile, carbon tetrachloride, chloroform and ether are suitable as the solvent. It is preferred to carry out the reaction at a temperature of 20° to 100° C., especially at 25° to 60° C. When the starting compound (VII) is lower alkyl trans-3-(4-methoxyphenyl)glycidate, the threo isomer of the compound (XI) is obtained.

The hydrolysis of the compound (XI) can be conducted by treating said compound with an alkali agent in a solvent. The alkali agent includes, for example, sodium hydroxide, potassium hydroxide, sodium carbonate and potassium carbonate. A mixture of water and lower alkanol (e.g., methanol, ethanol, propanol), dimethylsulfoxide or dimthylformamide is suitable as the solvent. It is preferred to carry out the reaction at a temperature of 0° to 80° C., especially at 20° to 40° C.

If required, the compound (XII) thus obtained may be optically resolved into each optically active enantiomers by using an optically active resolving agent such as optically active isomer of lysine. For example, the optical resolution of (±)-threo-2-hydroxy-3-(2-nitro-5-chlorophenylthio)-3-(4-methoxyphenyl)-propionic acid can be accomplished by the steps of reacting said compound with an optically active lysine to form the diastereoisomeric salts thereof, and separating the diastereoisomeric salts from each other by selective crystallization. (+)-Threo-2-hydroxy-3-(2-nitro-5-chlorophenylthio)-3-(4-methoxyphenyl)propionic acid forms the less soluble diastereoisomeric salt if L-lysine is used as the resolving agent, and, on the other hand, (−)-threo-2-hydroxy-3-(2-nitro-5-chlorophenylthio)-3-(4-methoxyphenyl)propionic acid forms the less soluble diastereoisomeric salt if D-lysine is used as the resolving agent. Selective crystallization is carried out by recrystallizing the diastereoisomeric salts from a solvent such as dimethylformamide of lower alkanol (e.g., methanol). After the optical resolution, the optically active compound (XII) in free form can be regenerated by treating the thus-obtained diastereoisomeric salt with an acid (e.g., hydrochloric acid, sulfuric acid).

The reduction of the thus-obtained racemic or optically active compound (XII) can be conducted by subjecting said compound to catalytic hydrogenation or treating said compound with a metal or a metal salt and an acid. The catalytic hydrogenation of the compound (XII) is carried out in the presence of a catalyst in hydrogen gas atmosphere in a solvent. The catalyst includes, for example, palladiumcharcoal, palladium black, Raney nickel and Raney cobalt. Lower alkanol (e.g., methanol, ethanol, propanol), acetic acid, tetrahydrofuran, dioxane and a mixture thereof are suitable as the solvent. It is preferred to carry out the reaction at a temperature of 20° to 50° C. under one to 20 atmospheric pressure. On the other hand, the treatment of the compound (XII) with the metal or metal salt and the acid is carried out in a solvent. The metal or metal salt includes, for example, tin, zinc, iron, stannous chloride and ferrous sulfate. The acid includes, for example, hydrochloric acid, hydrobromic acid, acetic acid and propionic acid. Water, methanol, ethanol, acetic acid, ether, tetrahydrofuran and a mixture thereof are suitable as the solvent. It is preferred to carry out the reaction at a temperature of 20° to 80° C.

The intramolecular cyclization of the thus-obtained compound (IX) can be carried out in the same manner as described in Method B.

On the other hand, the starting compound (II) in which $R^1$ is a group of the formula: $R^4CO-$ (wherein $R^4$ is the same as defined above) is also novel and can be prepared by acylating the compound (II-a) with the compound of the formula: $R^4COOH$ (wherein $R^4$ is the same as defined above) or a reactive derivative thereof under the same conditions as employed in acylation of the compound (I-b).

All of the aforementioned reactions can be carried out without racemization.

The compound (I) of the invention can be used for pharmaceutical use either as the free base or as a pharmaceutically acceptable acid addition salt thereof. Pharmaceutically acceptable acid addition salts of the compound (I) are, for example, inorganic acid addition salts such as hydrochloride, hydrobromide, hydroiodide, perchlorate, sulfate or phosphate, or organic acid addition salts such as oxalate, maleate, fumarate, tartrate or methanesulfonate, and so forth. These salts may be prepared, for example, by neutralizing the compound (I) with an acid. The compound (I) or a pharmaceutically acceptable acid addition salt thereof can be administered either orally or parenterally. Further, the compound (I) or its salt may be used in the form of a pharmaceutical preparation containing the same compound in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparations may be in solid form such as tablets, pills, capsules or suppositories; or in liquid form such as solutions, suspensions or emulsions. Further, when administered parenterally, the pharmaceutical preparation may be used in the form of injections.

As mentioned hereinbefore, the compound (I) of the present invention has a potent hypotensive activity, a potent cerebral or coronary vasodilating activity, and a potent platelet aggregation-inhibiting activity. Therefore, the compound (I) is useful for the treatment, amelioration or prophylaxis of hypertension; cerebral diseases such as cerebral vasospasm or cerebral infarction; and heart diseases such as angina pectoris, arrhythmias or coronary or cardiac infarction in a warm-blooded animal including human being. Especially, since the compound (I) of the present invention shows stronger and longer-lasting therapeutic effects (i.e., hypotensive, cerebral and coronary vasodilating activities) and, at the same time, is lower in toxicity as compared with the 7-chloro-derivative (e.g., (±)-cis-2-(4-methoxyphenyl)-3-acetoxy-5-[2-(dimethylamino)ethyl]-7-chloro-2,3-dihydro-1,5-benzothiazepin-4(5H)-one) of U.S. Pat. No. 3,562,257, the compound (I) of the present invention is much more useful as a hypotensive agent or a cerebral or coronary vasodilator than the above-mentioned 7-chloro-derivative. Therapeutic dose of the compound (I) or its salt depends on route of administration, the age, weight and conditions of patients; and particular diseases to be treated. In general, however, it may be used at a dose of 0.05 to 10 mg/kg/day, especially at a dose of 0.5 to 10 mg/kg/day in the case of oral administration or at a dose of 0.05 to 2 mg/kg/day in the case of parenteral administration (e.g., intravenous injection).

Practically and presently preferred embodiments of the present invention are illustratively shown in the following lines. Throughout the specification and claims, the terms "lower alkyl", "lower alkanoyl" and "lower alkanoic acid" should be interpreted as referring to straight or branched alkyl of one to 5 carbon atoms, straight or branched alkanoyl of 2 to 6 carbon atoms and straight or branched alkanoic acid of 2 to 6 carbon atoms, respectively.

Concomitantly, throughout the specification and claims, the term "threo" means that the hydroxy and 2-amino-5-chlorophenylthio (or 2-nitro-5-chlorophenylthio) groups substituted at the 2- and 3-positions of propionic acid have threo-type configuration (i.e., said two groups are placed on opposite side of the central bond in the Fisher's projection formula).

EXPERIMENT 1

(Hypotensive activity)

A test compound (dose: 30 mg/kg) dissolved or suspended in water was administered orally to spontaneously hypertensive rats (SHR) (one group: 3 rats) fasted overnight. The systolic blood pressure of the rats was measured by the tail plethysmographic technique (The Journal of Laboratory and Clinical Medicine 78(1971), page 957). The hypotensive activity of the test compound was estimated at one or 4 hours after dosing and expressed as "−" if the decrease in blood pressure is less than 10 mm Hg; "+" if the decrease is not less than 10 mm Hg but less than 20 mm Hg; "++" if the decrease is not less than 20 mm Hg but less than 40 mm Hg; "+++" if the decrease is not less than 40 mm Hg but less than 60 mm Hg; or "++++" if the decrease is not less than 60 mm Hg.

The results are shown in the following Table 1.

TABLE 1

| Test compounds | Hypotensive activity A period of time after dosing | |
|---|---|---|
| | 1 hr | 4 hrs |
| (The compounds of the present invention) | | |
| (+)-cis-2-(4-methoxyphenyl)-3-acetoxy-5-[2-(dimethylamino)ethyl]-8-chloro-2,3-dihydro-1,5-benzothiazepin-4(5H)-one maleate | ++++ | ++++ |
| (±)-cis-2-(4-methoxyphenyl)-3-acetoxy-5-[2-(dimethylamino)ethyl]-8-chloro-2,3-dihydro-1,5-benzothiazepin-4(5H)-one hydrochloride | ++ | ++++ |
| (±)-cis-2-(4-methoxyphenyl)-3-acetoxy-5-[2-(N—methyl-N—ethylamino)ethyl]-8-chloro-2,3-dihydro-1,5-benzothiazepin-4(5H)-one hydrochloride | +++ | +++ |
| (known compound) | | |
| (±)-cis-2-(4-methoxyphenyl)-3-acetoxy-5-[2-(dimethylamino)ethyl]-7-chloro-2,3-dihydro-1,5-benzothiazepin-4(5H)-one hydrochloride | − | ++ |

EXPERIMENT 2

(Cerebral vasodilating activity)

Male dogs weighing 10 to 20 kg were anesthetized with sodium pentobarbital (30 mg/kg, intravenous injection). The blood flow in vertebral artery was measured continuously by means of an electromagnetic flowmeter under artificial respiration. A test compound dissolved in an aqueous 5% glucose solution was injected into vertebral artery. The cerebral vasodilating activity of the test compound was estimated in terms of the potency ratio of said compound to papaverine, which was calculated from the dose-response curves thereof.

The results are shown in the following Table 2.

TABLE 2

| Test compounds | Cerebral vasodilating activity (potency ratio) |
|---|---|
| (The compounds of the present invention) | |
| (+)-cis-2-(4-methoxyphenyl)-3-acetoxy-5-[2-(dimethylamino)ethyl]-8-chloro-2,3-dihydro-1,5-benzothiazepin-4(5H)—one hydrochloride | 25 |
| (+)-cis-2-(4-methoxyphenyl)-3-propionyloxy-5-[2-(dimethylamino)ethyl]-8-chloro-2,3-dihydro-1,5-benzothiazepin-4(5H)—one oxalate | 23.7 |
| (Known compound) | |
| (±)-cis-2-(4-methoxyphenyl)-3-acetoxy-5-[2-(dimethylamino)ethyl]-7-chloro-2,3-dihydro-1,5-benzothiazepin-4(5H)—one hydrochloride | 5 |
| (Positive control) | |
| Papaverine | 1 |

EXPERIMENT 3

Male dogs weighing about 20–24 kg (one group: 2 dogs) were anesthetized with sodium pentobarbital (35 mg/kg, intravenous injection). The blood flow in vertebral artery was measured by means of an electromagnetic flowmeter under artificial respiration. A test compound (i.e., (+)-cis-2-(4-methoxyphenyl)-3-acetoxy-5-[2-(dimethylamino)ethyl]-8-chloro-2,3-dihydro-1,5-benzothiazepin-4(5H)-one hydrochloride) in a physiological saline solution was injected into the femoral vein at a dose of 200 µg/kg. The cerebral vasodilating activity of the test compound was estimated in terms of "increase (Δml/minute) in vertebral artery blood flow" which was calculated by subtracting "the blood flow measured immediately before injection of test compound" from "the blood flow measured at a period of time after injection of test compound".

The results are shown in the following Table 3.

TABLE 3

| Period of time after injection of test compound (minute) | Increase in vertebral artery blood flow (Δml/minute) |
|---|---|
| 1 | 58 |
| 3 | 53 |
| 5 | 52 |
| 10 | 38 |
| 20 | 21 |
| 30 | 14 |

EXPERIMENT 4

(Coronary vasodilating activity)

Langendorff's method was used for testing the effect on the coronary blood flow of the isolated heart of guinea pig (about 280 g). The isolated heart was perfused with Locke-Ringer solution containing 2% of defibrinated rabbit blood, which had been saturated with a mixed gas of 95% $O_2$ and 5% $CO_2$ (30° C.). Perfusion pressure was kept at 40 cm $H_2O$. A solution of a test compound in an aqueous 5% glucose solution was injected into the perfusing solution at a volume of 0.1 ml per heart. The overflow of the perfusate was measured by means of a drop counter.

The coronary vasodilating activity of the test compound was expressed as "±" if the increase in coronary blood flow is less than 0.5 ml/minute at a dose of 100 μg/heart; "+" if the increase is not less than 0.5 ml/minute at a dose of 100 μg/heart; "++" if the increase is not less than 0.5 ml/minute at a dose of 30 μg/heart; and "+++" if the increase is not less than 0.5 ml/minute at a dose of not more than 10 μg/heart.

The results are shown in the following Table 4.

TABLE 4

| Test compounds | Coronary vasodilating activity |
|---|---|
| (The compounds of the present invention) | |
| (+)-cis-2-(4-methoxyphenyl)-3-acetoxy-5-[2-(dimethylamino)ethyl]-8-chloro-2,3-dihydro-1,5-benzothiazepin-4(5H)—one hydrochloride | +++ |
| (±)-cis-2-(4-methoxyphenyl)-3-acetoxy-5-[2-(dimethylamino)ethyl]-8-chloro-2,3-dihydro-1,5-benzothiazepin-4(5H)—one hydrochloride | +++ |
| (±)-cis-2-(4-methoxyphenyl)-3-acetoxy-5-[2-(N—methyl-N—n-propylamino)ethyl]-8-chloro-2,3-dihydro-1,5-benzothiazepin-4(5H)—one oxalate | +++ |
| (Positive control) | |
| Papaverine | + |

EXPERIMENT 5

(Platelet aggregation-inhibiting activity)

Blood was collected from the abdominal aorta of male Sprague-Dawley rats which were anesthetized with ether. Nine volumes of rat blood were mixed with one volume of an aqueous trisodium citrate solution, and the mixture was centrifuged to give platelet-rich plasma ("PRP") as the supernatant solution. The bottom layer was further centrifuged to give platelet-poor plasma ("PPP") as the supernatant solution. Platelet counts were adjusted to $0.8-1 \times 10^6/mm^3$ for PRP by dilution with PPP. After a mixture of 200 μl of the diluted PRP and 25 μl of a test compound solution (final concentration: 100 μg/ml) was stirred for 2 minutes at 37° C., 25 μl of a collagen solution [Biochim. Biophys. Acta, 186, page 254(1969)] were added thereto. The degree of platelet aggregation was estimated by Born's method [Nature, 194, page 927(1962)] and the percentage inhibition of platelet aggregation was calculated therefrom. The platelet aggregation-inhibiting activity of the test compound was expressed as (−) if the test compound showed less than 10% inhibition of platelet aggregation; (+) if the test compound showed not less than 10% inhibition of platelet aggregation but said percentage inhibition was lower than that of acetylsalicylic acid (100 μg/ml); or (++) if the test compound showed the platelet aggregation-inhibiting activity at least as strong as that of acetylsalicylic acid (100 μg/ml).

The results are shown in the following Table 5.

TABLE 5

| Test compounds | Platelet aggregation-inhibiting activity |
|---|---|
| (The compounds of the present invention) | |
| (±)-cis-2-(4-methoxyphenyl)-3-acetoxy-5-[2-(dimethylamino)ethyl]-8-chloro-2,3-dihydro-1,5-benzothiazepin-4(5H)—one hydrochloride | ++ |
| (+)-cis-2-(4-methoxyphenyl)-3-hydroxy-5-[2-(dimethylamino)ethyl]-8-chloro-2,3-dihydro-1,5-benzothiazepin-4(5H)—one oxalate | ++ |
| (+)-cis-2-(4-methoxyphenyl)-3-acetoxy-5-[2-(diethylamino)ethyl]-8-chloro-2,3-dihydro-1,5-benzothiazepin-4(5H)—one oxalate | ++ |
| (±)-cis-2-(4-methoxyphenyl)-3-acetoxy-5-[2-(N—methyl-N—n-propylamino)ethyl]-8-chloro-2,3-dihydro-1,5-benzothiazepin-4(5H)—one oxalate | ++ |
| (+)-cis-2-(4-methoxyphenyl)-3-propionyloxy-5-[2-(dimethylamino)ethyl]-8-chloro-2,3-dihydro-1,5-benzothiazepin-4(5H)—one oxalate | ++ |

EXAMPLE 1

A mixture of 6.8 g of (+)-cis-2-(4-methoxyphenyl)-3-hydroxy-8-chloro-2,3-dihydro-1,5-benzothiazepin-4(5H)-one, 3.02 g of 2-(dimethylamino)ethyl chloride hydrochloride, 6.1 g of potassium carbonate and 150 ml of acetone is refluxed for 20 hours. After the reaction is completed, insoluble materials are removed by filtration and washed with ethanol. The washings are added to the filtrate, and the combined solution is evaporated under reduced pressure to remove solvent. The residue is dissolved in ethyl acetate, and the solution is washed with water, dried and then evaporated to remove solvent. The residue is recrystallized from a mixture of ethyl acetate and n-hexane. 7.13 g of (+)-cis-2-(4-methoxyphenyl)-3-hydroxy-5-[2-(dimethylamino)ethyl]-8-chloro-2,3-dihydro-1,5-benzothiazepin-4(5H)-one are thereby obtained as colorless needles.

M.p. 122°–124° C. (decomp.)

$[\alpha]_D^{20} + 144.6°$ (C=0.85, methanol)

Oxalate:

M.p. 201°–203° C. (decomp.) (recrystallized from a mixture of chloroform, ethanol and ether)

$[\alpha]_D^{20} + 78.4°$ (C=0.74, dimethylformamide)

EXAMPLE 2

A mixture of 6.4 g of (+)-cis-2-(4-methoxyphenyl)-3-hydroxy-5-[2-(dimethylamino)ethyl]-8-chloro-2,3-dihydro-1,5-benzothiazepin-4(5H)-one, 65 ml of acetic anhydride and 0.7 ml of pyridine is stirred at 110° C. for 3 hours. After the reaction is completed, the reaction mixture is evaporated to remove solvent. The residue is converted to its hydrochloride and recrystallized from a mixture of acetone and ethanol. 4.7 g of (+)-cis-2-(4-methoxyphenyl)-3-acetoxy-5-[2-(dimethylamino)ethyl]-8-chloro-2,3-dihydro-1,5-benzothiazepin-4(5H)-one hydrochloride are thereby obtained.

M.p. 127°–131° C. (decomp.)

$[\alpha]_D^{20} + 92.2°$ (C=0.796, ethanol)

Analysis calculated for $C_{22}H_{25}O_4N_2SCl.HCl.\frac{1}{2}H_2O$ C, 53.44; H, 5.50; N, 5.67; Cl, 14.34 Found: C, 53.11; H, 5.38; N, 5.60; Cl, 13.98

Maleate:
Needles (recrystallized from ethanol)
M.p. 158°–160° C.
$[\alpha]_D^{20} + 75.4°$ (C=1.0, methanol)

Fumarate:
Needles (recrystallized from a mixture of ethanol and ether)
M.p. 199°–201° (decomp.)

Methanesulfonate:
Prisms (recrystallized from a mixture of ethanol and ether)
M.p. 147°–149° C.

Analysis calculated for $C_{23}H_{29}O_7N_2S_2Cl.H_2O$ C, 49.05; H, 5.55; N, 4.62; S, 11.38; Cl, 6.29 Found: C, 48.88; H, 5.42; N, 5.03; S, 11.38; Cl, 6.38

EXAMPLE 3

A mixture of 6.4 g of (−)-cis-2-(4-methoxyphenyl)-3-hydroxy-8-chloro-2,3-dihydro-1,5-benzothiazepin-4(5H)-one, 3.0 g of 2-(dimethylamino)ethyl chloride hydrochloride, 5.8 g of potassium carbonate and 150 ml of acetone is treated in the same manner as described in Example 1. The crude product thus obtained as recrystallized from a mixture of ethyl acetate and n-hexane. 6.93 g of (−)-cis-2-(4-methoxyphenyl)-3-hydroxy-5-[2-(dimethylamino)ethyl]-8-chloro-2,3-dihydro-1,5-benzothiazepin-4(5H)-one are thereby obtained as colorless needles.

M.p. 121°–123° (decomp.)

$[\alpha]_D^{20} - 142.7°$ (C=1.04, methanol)

Oxalate:
M.p. 202°–204° C. (decomp.) (recrystallized from a mixture of chloroform, ethanol and ether)
$[\alpha]_D^{20} - 78.4°$ (C=0.88, dimethylformamide)

EXAMPLE 4

A mixture of 6.35 g of (−)-cis-2-(4-methoxyphenyl)-3-hydroxy-5-[2-(dimethylamino)ethyl]-8-chloro-2,3-dihydro-1,5-benzothiazepin-4(5H)-one, 65 ml of acetic anhydride and 0.7 ml of pyridine is treated in the same manner as described in Example 2. The product is converted to its hydrochloride and recrystallized from acetone. 4.28 g of (−)-cis-2-(4-methoxyphenyl)-3-acetoxy-5-[2-(dimethylamino)ethyl]-8-chloro-2,3-dihydro-1,5-benzothiazepin-4(5H)-one hydrochloride are thereby obtained.

M.p. 128°–132° C. (decomp.)

$[\alpha]_D^{20} - 93.3°$ (C=0.872, ethanol)

Analysis calculated for $C_{22}H_{25}O_4N_2SCl.HCl.\frac{1}{2}H_2O$ C, 53.44; H, 5.50; N, 5.67; Cl, 14.34 Found: C, 53.17; H, 5.45; N, 5.59; Cl, 14.28

EXAMPLE 5

A mixture of 6.72 g of (±)-cis-2-(4-methoxyphenyl)-3-hydroxy-8-chloro-2,3-dihydro-1,5-benzothiazepin-4(5H)-one, 2.58 g of potassium hydroxide and 90 ml of dimethylsulfoxide is stirred at room temperature for one hour. Then, 3.16 g of 2-(dimethylamino)ethyl chloride hydrochloride are added to the mixture, and said mixture is stirred at room temperature for 16 hours. The reaction mixture is poured into ice-water, and the precipitated crystals are collected by filtration and washed with water. The crystals are dissolved in concentrated hydrochloric acid, and the solution is washed with ethyl acetate and then alkalized with potassium carbonate. Then, the solution is extracted with chloroform. The extract is washed with water, dried and then evaporated to remove solvent. The residue is converted to its hydrochloride and then recrystallized from ethanol. 6.65 g of (±)-cis-2-(4-methoxyphenyl)-3-hydroxy-5-[2-(dimethylamino)ethyl]-8-chloro-2,3-dihydro-1,5-benzothiazepin-4(5H)-one hydrochloride are thereby obtained. Recrystallization of the product from a mixture of chloroform, ethanol and ether gives crystals (prisms) melting at 136°–139° C.

Analysis calculated for $C_{20}H_{23}O_3N_2SCl.HCl.\frac{1}{2}C_2H_5OH$ C, 53.96; H, 5.82; N, 5.99; Cl, 15.17 Found: C, 53.61; H, 5.94; N, 6.00; Cl, 15.31

EXAMPLE 6

A mixture of 1 g of (±)-cis-2-(4-methoxyphenyl)-3-hydroxy-5-[2-(dimethylamino)ethyl]-8-chloro-2,3-dihydro-1,5-benzothiazepin-4(5H)-one hydrochloride, 2 ml of acetic anhydride and 2 ml of acetic acid is stirred at 110° C. for 4 hours. Then, the reaction mixture is evaporated under reduced pressure to remove solvent. Ether is added to the residue, and the precipitated crystals are collected by filtration. 1.08 g of (±)-cis-2-(4-methoxyphenyl)-3-acetoxy-5-[2-(dimethylamino)ethyl]-8-chloro-2,3-dihydro-1,5-benzothiazepin-4(5H)-one hydrochloride are thereby obtained. Recrystallization of the product from a mixture of chloroform, ethanol and ether gives crystals (needles) melting at 159°–161° C.

Analysis calculated for $C_{22}H_{25}N_2O_4SCl.HCl.C_2H_5OH$ C, 54.23; H, 5.88; N, 5.27; Cl, 13.34 Found: C, 53.99; H, 5.70; N, 5.47; Cl, 13.45

EXAMPLE 7

3 g of (±)-cis-2-(4-methoxyphenyl)-3-hydroxy-8-chloro-2,3-dihydro-1,5-benzothiazepin-4(5H)-one and 1.7 g of 2-(N-methyl-N-ethylamino)ethyl chloride hydrochloride are treated in the same manner as described in Example 5. The product is converted to its hydrochloride and recrystallized from a mixture of ethanol and ether. 3.1 g of (±)-cis-2-(4-methoxyphenyl)-3-hydroxy-5-[2-(N-methyl-N-ethylamino)ethyl]-8-chloro-2,3-dihydro-1,5-benzothiazepin-4(5H)-one hydrochloride are thereby obtained as colorless needles.

M.p. 132°–135° C. (decomp.)

Analysis calculated for $C_{21}H_{25}O_3N_2SCl.HCl.\frac{1}{2}H_2O$ C, 54.07; H, 5.84; N, 6.01; Cl, 15.20 Found: C, 54.32; H, 5.88; N, 5.76; Cl, 15.31

EXAMPLE 8

A mixture of 0.9 g of (±)-cis-2-(4-methoxyphenyl)-3-hydroxy-5-[2-(N-methyl-N-ethylamino)ethyl]-8-chloro- 2,3-dihydro-1,5-benzothiazepin-4(5H)-one hydrochloride, 5 ml of acetic anhydride and 5 ml of acetic acid is treated in the same manner as described in Example 6. The crude product thus obtained is recrystallized from a mixture of chloroform, ethanol and ether. 0.9 g of (±)-cis-2-(4-methoxyphenyl)-3-acetoxy-5-[2-(N-methyl-N-ethylamino)ethyl]-8-chloro-2,3-dihydro-1,5-benzothiazepin-4(5H)-one hydrochloride is thereby obtained as needles.

M.p. 229°–232° C. (decomp.)

Analysis calculated for $C_{23}H_{27}N_2O_4SCl\cdot HCl\cdot\frac{1}{2}H_2O$ C, 54.22; H, 5.75; N, 5.51; Cl, 13.95 Found: C, 53.97; H, 5.82; N, 5.87; Cl, 13.73

EXAMPLE 9

2 g of (±)-cis-2-(4-methoxyphenyl)-3-hydroxy-8-chloro-2,3-dihydro-1,5-benzothiazepin-4(5H)-one and 1.13 g of 2-(N-methyl-N-n-propylamino)ethyl chloride hydrochloride are treated in the same manner as described in Example 5. The product is converted to its hydrobromide and recrystallized from a mixture of ethanol and ether. 2.1 g of (±)-cis-2-(4-methoxyphenyl)-3-hydroxy-5-[2-(N-methyl-N-n-propylamino)ethyl]-8-chloro-2,3-dihydro-1,5-benzothiazepin-4(5H)-one hydrobromide are thereby obtained as colorless prisms.

M.p. 82°–83° C. (decomp.)

EXAMPLE 10

A mixture of 0.82 g of (±)-cis-2-(4-methoxyphenyl)-3-hydroxy-5-[2-(N-methyl-N-n-propylamino)ethyl]-8-chloro-2,3-dihydro-1,5-benzothiazepin-4(5H)-one, 10 ml of acetic anhydride and 1 ml of pyridine is stirred at 100° C. for 3 hours. Then, the reaction mixture is evaporated to remove solvent. The residue is converted to its oxalate and recrystallized from a mixture of chloroform and ethanol. 0.75 g of (±)-cis-2-(4-methoxyphenyl)-3-acetoxy-5-[2-(N-methyl-N-n-propylamino)ethyl]-8-chloro-2,3-dihydro-1,5-benzothiazepin-4(5H)-one oxalate is obtained as colorless needles.

M.p. 197°–198° C. (decomp.)

EXAMPLE 11

A mixture of 3.4 g of (+)-cis-2-(4-methoxyphenyl)-3-acetoxy-8-chloro-2,3-dihydro-1,5-benzothiazepin-4(5H)-one, 1.5 g of 2-(dimethylamino)ethyl chloride hydrochloride, 3.23 g of potassium carbonate and 80 ml of acetone is treated in the same manner as described in Example 1. The product thus obtained is converted into its hydrochloride and recrystallized from a mixture of acetone and ethanol. 3.75 g of (+)-cis-2-(4-methoxyphenyl)-3-acetoxy-5-[2-(dimethylamino)ethyl]-8-chloro-2,3-dihydro-1,5-benzothiazepin-4(5H)-one hydrochloride are thereby obtained.

M.p. 127°–131° C. (decomp.)

$[\alpha]_D^{20}+92.4°$ (c=0.81, ethanol)

EXAMPLE 12

A mixture of 3.2 g of (±)-cis-2-(4-methoxyphenyl)-3-acetoxy-8-chloro-2,3-dihydro-1,5-benzothiazepin-4(5H)-one, 1.46 g of 2-(dimethylamino)ethyl chloride hydrochloride, 3 g of potassium carbonate and 75 ml of acetone is treated in the same manner as described in Example 1. The product thus obtained is converted into its hydrochloride and recrystallized from a mixture of chloroform, ethanol and ether. 3.4 g of (±)-cis-2-(4-methoxyphenyl)-3-acetoxy-5-[2-(dimethylamino)ethyl]-8-chloro-2,3-dihydro-1,5-benzothiazepin-4(5H)-one hydrochloride are thereby obtained.

M.p. 159°–161° C.

EXAMPLE 13

A mixture of 1 g of (±)-cis-2-(4-methoxyphenyl)-3-acetoxy-8-chloro-2,3-dihydro-1,5-benzothiazepin-4(5H)-one, 0.5 g of 2-(N-methyl-N-ethylamino)ethyl chloride hydrochloride, 0.95 g of potassium carbonate and 20 ml of acetone is treated in the same manner as described in Example 1. The product thus obtained is converted into its hydrochloride and recrystallized from a mixture of chloroform, ethanol and ether. 1.03 g of (±)-cis-2-(4-methoxyphenyl)-3-acetoxy-5-[2-(N-methyl-N-ethylamino)ethyl]-8-chloro-2,3-dihydro-1,5-benzothiazepin-4(5H)-one hydrochloride are thereby obtained.

M.p. 229°–232° C. (decomp.)

EXAMPLE 14

A mixture of 1 g of (±)-cis-2-(4-methoxyphenyl)-3-acetoxy-8-chloro-2,3-dihydro-1,5-benzothiazepin-4(5H)-one, 0.55 g of 2-(N-methyl-N-n-propylamino)ethyl chloride hydrochloride, 0.95 g of potassium carbonate and 20 ml of acetone is treated in the same manner as described in Example 1. The product thus obtained is converted into its oxalate and recrystallized from a mixture of chloroform and ethanol. 1.1 g of (±)-cis-2-(4-methoxyphenyl)-3-acetoxy-5-[2-(N-methyl-N-n-propylamino)ethyl]-8-chloro-2,3-dihydro-1,5-benzothiazepin-4(5H)-one oxalate are thereby obtained as colorless needles.

M.p. 197°–198° C. (decomp.)

EXAMPLE 15

A mixture of 2.5 g of (+)-cis-2-(4-methoxyphenyl)-3-hydroxy-8-chloro-2,3-dihydro-1,5-benzothiazepin-4(5H)-one, 1.3 g of 2-(N-methyl-N-ethylamino)ethyl chloride hydrochloride, 3.01 g of potassium carbonate and 35 ml of acetone is refluxed for 21 hours. Insoluble materials are filtered off, and the filtrate is evaporated under reduced pressure to remove solvent. The residue is converted into its perchlorate and then recrystallized from methanol. 3.24 g of (+)-cis-2-(4-methoxyphenyl)-3-hydroxy-5-[2-(N-methyl-N-ethylamino)ethyl]-8-chloro-2,3-dihydro-1,5-benzothiazepin-4(5H)-one perchlorate are obtained.

M.p. 197°–201° C.

$[\alpha]_D^{20}+80.6°$ (C=0.5, methanol)

EXAMPLE 16

A mixture of 2.74 g of (+)-cis-2-(4-methoxyphenyl)-3-hydroxy-5-[2-(N-methyl-N-ethylamino)ethyl]-8-chloro-2,3-dihydro-1,5-benzothiazepin-4(5H)-one, 25 ml of acetic anhydride and 12 drops of pyridine is heated at a temperature of 100° C. for 3 hours. The mixture is evaporated under reduced pressure to remove solvent. The residue is dissolved in ether, and the solution is extracted with diluted hydrochloric acid. The extract is washed with ether, alkalized with an aqueous 10% sodium hydroxide solution, and then extracted with chloroform. The chloroform solution is washed with water, dried and then evaporated under reduced pressure to remove solvent. The residue is converted into its L-tartrate and then recrystallized from ethanol. 3.28 g of (+)-cis-2-(4-methoxyphenyl)-3-acetoxy-5-[2-(N-methyl-N-ethylamino)ethyl]-8-chloro- 2,3-dihydro-1,5-benzothiazepin-4(5H)-one L-tartrate are obtained.

M.p. 128°–133° C. (decomp.)
$[\alpha]_D^{20}+84.0°$ (C=1.0, methanol)

EXAMPLE 17

A mixture of 1.01 g of (+)-cis-2-(4-methoxyphenyl)-3-hydroxy-8-chloro-2,3-dihydro-1,5-benzothiazepin-4(5H)-one, 0.57 g of 2-(diethylamino)ethyl chloride hydrochloride, 1.24 g of potassium carbonate and 30 ml of acetone is treated in the same manner as described in Example 15. The crude product is converted into its fumarate and then recrystallized from ethanol. 1.22 g of (+)-cis-2-(4-methoxyphenyl)-3-hydroxy-5-[2-(diethylamino)ethyl]-8-chloro-2,3-dihydro-1,5-benzothiazepin-4(5H)-one fumarate are obtained.

M.p. 146°–147.5° C.
$[\alpha]_D^{20}+91.0°$ (C=1.0, methanol)

EXAMPLE 18

A mixture of 0.67 g of (+)-cis-2-(4-methoxyphenyl)-3-hydroxy-5-[2-(diethylamino)ethyl]-8-chloro-2,3-dihydro-1,5-benzothiazepin-4(5H)-one, 7 ml of acetic anhydride and 2 drops of pyridine is treated in the same manner as described in Example 16. The crude product is converted into its oxalate and recrystallized from ethanol. 0.634 g of (+)-cis-2-(4-methoxyphenyl)-3-acetoxy-5-[2-(diethylamino)ethyl]-8-chloro-2,3-dihydro-1,5-benzothiazepin-4(5H)-one oxalate is obtained.

M.p. 183°–184.5° C. (decomp.)
$[\alpha]_D^{20}+86.6°$ (C=1.0, methanol)

EXAMPLE 19

A mixture of 0.8 g of (+)-cis-2-(4-methoxyphenyl)-3-hydroxy-5-[2-(dimethylamino)ethyl]-8-chloro-2,3-dihydro-1,5-benzothiazepin-4(5H)-one, 9 ml of formic acid, 3 ml of acetic anhydride and one ml of pyridine is stirred at room temperature for 3 days. The reaction mixture is evaporated under reduced pressure to remove solvent. The residue is converted into its oxalate and recrystallized from a mixture of ethanol and ether. 0.725 g of (+)-cis-2-(4-methoxyphenyl)-3-formyloxy-5-[2-(dimethylamino)ethyl]-8-chloro-2,3-dihydro-1,5-benzothiazepin-4(5H)-one oxalate is obtained.

M.p. 180°–183° C. (decomp.)
$[\alpha]_D^{20}+117.8°$ (C=1.0, dimethylformamide)

EXAMPLE 20

A mixture of one g of (+)-cis-2-(4-methoxyphenyl)-3-hydroxy-5-[2-(dimethylamino)ethyl]-8-chloro-2,3-dihydro-1,5-benzothiazepin-4(5H)-one, 0.47 g of propionyl chloride and 20 ml of pyridine is stirred at room temperature for 2 hours. The reaction mixture is evaporated under reduced pressure to remove solvent. The residue is converted into its oxalate and recrystallized from acetone. 0.947 g of (+)-cis-2-(4-methoxyphenyl)-3-propionyloxy-5-[2-(dimethylamino)ethyl]-8-chloro-2,3-dihydro-1,5-benzothiazepin-4(5H)-one oxalate is obtained.

M.p. 130° C. (decomp.)
$[\alpha]_D^{20}+85.82°$ (C=1, dimethylformamide)

EXAMPLE 21

A mixture of 900 mg of (+)-cis-2-(4-methoxyphenyl)-3-hydroxy-5-[2-(dimethylamino)ethyl]-8-chloro-2,3-dihydro-1,5-benzothiazepin-4(5H)-one, 300 mg of n-butyryl chloride and one ml of pyridine is treated in the same manner as described in Example 20. The crude product is converted into its oxalate and recrystallized from ethanol. 1.216 g of (+)-cis-2-(4-methoxyphenyl)-3-n-butyryloxy-5-[2-(dimethylamino)ethyl]-8-chloro-2,3-dihydro-1,5-benzothiazepin-4(5H)-one oxalate are obtained.

M.p. 140°–142° C.
$[\alpha]_D^{20}+61.28°$ (C=0.320, methanol)

EXAMPLE 22

A mixture of 900 mg of (+)-cis-2-(4-methoxyphenyl)-3-hydroxy-5-[2-(dimethylamino)ethyl]-8-chloro-2,3-dihydro-1,5-benzothiazepin-4(5H)-one, 300 mg of n-valeryl chloride and one ml of pyridine is treated in the same manner as described in Example 20. The crude product is converted into its oxalate and recrystallized from ethanol. 1.218 g of (+)-cis-2-(4-methoxyphenyl)-3-n-valeryloxy-5-[2-(dimethylamino)ethyl]-8-chloro-2,3-dihydro-1,5-benzothiazepin-4(5H)-one oxalate are obtained.

M.p. 167°–169° C.
$[\alpha]_D^{20}+56.4°$ (C=0.328, methanol)

EXAMPLE 23

A mixture of 1.5 g of (+)-cis-2-(4-methoxyphenyl)-3-hydroxy-5-[2-(dimethylamino)ethyl]-8-chloro-2,3-dihydro-1,5-benzothiazepin-4(5H)-one, 0.22 g of sodium hydride (62.2% oil dispersion) and 45 ml of benzene is refluxed for one hour. After cooling, 0.53 g of dimethyl sulfate is added to the mixture, and the mixture is stirred at room temperature for 68 hours. The mixture is further stirred at 50° C. for 3 hours. The reaction mixture is washed with an aqueous 10% sodium hydroxide solution and water, successively. The washed solution is dried and evaporated under reduced pressure to remove solvent. The residue is purified by silica gel chromatography (solvent, chloroform:ethanol (9:1)), converted into its hydrochloride and then recrystallized from a mixture of ethanol and ether. 0.7 g of (+)-cis-2-(4-methoxyphenyl)-3-methoxy-5-[2-(dimethylamino)ethyl]-8-chloro-2,3-dihydro-1,5-benzothiazepin-4(5H)-one hydrochloride is obtained.

M.p. 212°–216° C. $[\alpha]_D^{20}+89.16°$ (C=1.0, dimethylformamide)

PREPARATION OF STARTING COMPOUND

Preparation 1

A mixture of 20.3 g of 2-amino-5-chlorothiophenol and 26.4 g of methyl (±)-trans-3-(4-methoxyphenyl)-glycidate is stirred at 160° C. for 16 hours under argon atmosphere. After cooling, ethanol is added to the reaction mixture, and the precipitated crystals are collected by filtration and washed with ethanol. 11.3 g of (±)-cis-2-(4-methoxyphenyl)-3-hydroxy-8-chloro-2,3-dihydro-1,5-benzothiazepin-4(5H)-one are thereby obtained. M.p. 230°–232° C. Recrystallization of the product from dimethylformamide gives crystals (needles) melting at 230°–232° C.

The mother liquor (ethanol solution) is evaporated under reduced pressure to remove solvent. The residue is dissolved in ethyl acetate, and the solution is washed with 10% hydrochloric acid, water, an aqueous saturated sodium bicarbonate solution and water, successively. Then, the solution is dried and evaporated to remove solvent. The residue is purified by silica gel chromatography (solvent: chloroform). 0.8 g of (±)-cis-2-(4-methoxyphenyl)-3-hydroxy-8-chloro-2,3-dihydro-1,5-benzothiazepin-4(5H)-one (cis-isomer) and 1.5 g of (±)-trans-2-(4-methoxyphenyl)-3-hydroxy-8- chloro-2,3-dihydro-1,5-benzothiazepin-4(5H)-one (trans-isomer) are obtained, respectively.
Cis-isomer:
M.p. 230°–232° C.
Trans-isomer:
Needles (recrystallized from a mixture of ethyl acetate and n-hexane)
M.p. 183°–185° C.

Preparation 2

(1) A mixture of 63.1 g of 2-amino-5-chlorothiophenol, 90.4 g of methyl (±)-trans-3-(4-methoxyphenyl)glycidate and 600 ml of toluene is stirred at 65° to 75° C. for 40 hours. After cooling, the precipitated crystals are collected by filtration. 71.7 g of methyl (±)-threo-2-hydroxy-3-(2-amino-5-chlorophenylthio)-3-(4-methoxyphenyl)propionate are thereby obtained. M.p. 131°–132° C. Recrystallization of the product from a mixture of ethyl acetate and n-hexane gives crystals (needles) melting at 131°–132° C.

(2) A mixture of 23.5 g of methyl (±)-threo-2-hydroxy-3-(2-amino-5-chlorophenylthio)-3-(4-methoxyphenyl)propionate, 150 ml of an aqueous 5% sodium hydroxide solution and 150 ml of methanol is stirred at room temperature for 2 hours. The reaction mixture is adjusted to pH 4 with diluted hydrochloric acid, and the precipitated crystals are collected by filtration. The crystals are washed with water and recrystallized from a mixture of dimethylformamide and ethanol. 17.5 g of (±)-threo-2-hydroxy-3-(2-amino-5-chlorophenylthio)-3-(4-methoxyphenyl)propionic acid are thereby obtained as needles. M.p. 189°–191° C. (decomp.)

(3) A mixture of 2 g of (±)-threo-2-hydroxy-3-(2-amino-5-chlorophenylthio)3-(4-methoxyphenyl)propionic acid and 150 ml of xylene is refluxed for 25 hours while removing the resulting water by a dehydration apparatus. After cooling, the precipitated crystals are collected by filtration and recrystallized from dimethylformamide. 1.6 g of (±)-cis-2-(4-methoxyphenyl)-3-hydroxy-8-chloro-2,3-dihydro-1,5-benzothiazepin-4(5H)-one are thereby obtained. M.p. 230°–232° C.

Preparation 3

450 mg of methyl (±)-threo-2-hydroxy-3-(2-amino-5-chlorophenylthio)-3-(4-methoxyphenyl)propionate are dissolved in 1.5 ml of dimethylsulfoxide, and the solution is added to a methylsulfinylcarbanion solution (prepared from 3 ml of dimethylsulfoxide and 103 mg of 60% sodium hydride in oil dispersion) at a temperature below 15° C. The mixture is stirred at room temperature for 40 minutes. Then, the mixture is poured into 190 mg of acetic acid and ice. Crystalline precipitates are collected by filtration, washed with water, dried and then recrystallized from dimethylformamide. 300 mg of (±)-cis-2-(4-methoxyphenyl)-3-hydroxy-8-chloro-2,3-dihydro-1,5-benzothiazepin-4(5H)-one are obtained.

The physico-chemical properties of this product are identical with those of the product obtained in Preparation 2-(3).

Preparation 4

(1) 30.5 g of L-p-hydroxyphenylglycine methyl ester hydrochloride are dissolved in 600 ml of methanol, and a solution of 7.85 g of potassium hydroxide in 150 ml of methanol is added thereto. Insoluble materials are removed by filtration. A solution of 24.7 g of (±)-threo-2-hydroxy-3-(2-amino-5-chlorophenylthio)-3-(4-methoxyphenyl)propionic acid in 900 ml of methanol is added to the filtrate, and the mixture is evaporated at a temperature below 60° C. under reduced pressure to remove methanol. The residue is dissolved in 500 ml of ethanol, and insoluble materials are removed by filtration. The filtrate is allowed to stand at room temperature overnight, and insoluble materials are removed by filtration. The filtrate is evaporated under reduced pressure to remove solvent, and the residue is recrystallized from ethanol (the mother liquor is hereinafter referred to as "mother liquor (I)"). The thus-obtained crystals are further recrystallized from ethanol. 14.3 g of (+)-threo-2-hydroxy-3-(2-amino-5-chlorophenylthio)-3-(4-methoxyphenyl)propionic acid.L-p-hydroxyphenylglycine methyl ester salt are thereby obtained.
M.p. 169°–172° C. (decomp.)
$[\alpha]_D^{20} +316.7°$ (C=1.14, dimethylformamide)

The product (14.3 g) obtained above is acidified by adding 10% hydrochloric acid, and the aqueous mixture is evaporated under reduced pressure to remove solvent. Water is added to the residue, and the precipitated crystals are collected by filtration, washed with water and then dried. 7.8 g of (+)-threo-2-hydroxy-3-(2-amino-5-chlorophenylthio)-3-(4-methoxyphenyl)propionic acid are thereby obtained.
M.p. 173°–175° C. (decomp.)
$[\alpha]_D^{20} +325.0°$ (C=0.73, N-NaOH)

The mother liquor (I) obtained above is evaporated under reduced pressure. The residue is acidified by adding 10% hydrochloric acid, and water is added thereto. The precipitated crystals are collected by filtration. The thus-obtained crystals (15.5 g), 4.92 g of potassium hydroxide and 19.1 g of D-p-hydroxyphenylglycine methyl ester hydrochloride are treated in the same manner as described above. 13.9 g of (−)-threo-2-hydroxy-3-(2-amino-5-chlorophenylthio)-3-(4-methoxyphenyl)propionic acid.D-p-hydroxyphenylglycine methyl ester salt are thereby obtained.
M.p. 168°–171° C. (decomp.)
$[\alpha]_D^{20} -316.5°$ (C=1.342, dimethylformamide)

The product (13.9 g) obtained above is converted to its free acid by using 10% hydrochloric acid in the same manner as described above. 7.3 g of (−)-threo-2-hydroxy-3-(2-amino-5-chlorophenylthio)-3-(4-methoxyphenyl)propionic acid are thereby obtained.
M.p. 172°–174° C. (decomp.)
$[\alpha]_D^{20} -323.4°$ (C=0.93, N-NaOH)

(2-a) A mixture of 10 g of (+)-threo-2-hydroxy-3-(2-amino-5-chlorophenylthio)-3-(4-methoxyphenyl)propionic acid and 600 ml of xylene is refluxed for 20 hours. After cooling, the precipitated crystals are collected by filtration. 6.9 g of (+)-cis-(4-methoxyphenyl)-3-hydroxy-8-chloro-2,3-dihydro-1,5-benzothiazepin-4(5H)-one are thereby obtained.
M.p. 236°–239° C. (decomp.)
$[\alpha_D^{20} +92.1°$ (C=1.02, dimethylformamide)

(2-b) A mixture of 9 g of (−)-threo-2-hydroxy-3-(2-amino-5-chlorophenylthio)-3-(4-methoxyphenyl)propionic acid and 500 ml of xylene is treated in the same manner as described in paragraph (2-a). 6.5 g of (−)-cis-2-(4-methoxyphenyl)-3-hydroxy-8-chloro-2,3-dihydro-1,5-benzothiazepin-4(5H)-one are thereby obtained.
M.p. 235°–237° C. (decomp.)
$[\alpha]_D^{20} -92.0°$ (C=1.06, dimethylformamide)

Preparation 5

(1-a) 19.75 g of 2-nitro-5-chlorothiophenol and 27.6 g of methyl (±)-trans-3-(4-methoxyphenyl)glycidate are suspended in 200 ml of toluene, and 500 mg of zinc acetate dihydrate are added thereto. The mixture is stirred at room temperature for 3 hours. The mixture is evaporated under reduced pressure to remove solvent. Isopropyl ether is added to the residue and crystalline precipitates are collected therefrom. The crystals are washed with water and isopropyl ether and then recrystallized from a mixture of benzene and isopropyl ether. 27.66 g of methyl (±)-threo-2-hydroxy-3-(2-nitro-5-chlorophenylthio)-3-(4-methoxyphenyl)-propionate are obtained as needles.

M.p. 141°–143° C.

(1-b) 1.7 g of 2-nitro-5-chlorothiophenol, 2.38 g of methyl (±)-trans-3-(4-methoxyphenyl)glycidate, 17 ml of toluene and 0.05 ml of anhydrous stannic chloride are treated in the same manner as described in paragraph (1-a), whereby 2.21 g of methyl (±)-threo-2-hydroxy-3-(2-nitro-5-chlorophenylthio)-3-(4-methoxyphenyl)propionate are obtained.

M.p. 141°–143° C.

(1-c) 1.7 g of 2-nitro-5-chlorothiophenol, 2.38 g of methyl (±)-trans-3-(4-methoxyphenyl)glycidate, 17 ml of toluene and 30 mg of stannous chloride are treated in the same manner as described in paragraph (1-a), whereby 1.933 g of methyl (±)-threo-2-hydroxy-3-(2-nitro-5-chlorophenylthio)-3-(4-methoxyphenyl)propionate are obtained.

M.p. 141°–143° C.

(1-d) 1.7 g of 2-nitro-5-chlorothiophenol, 2.38 g of methyl (±)-trans-3-(4-methoxyphenyl)glycidate, 20 ml of toluene and 0.05 ml of stannous octylate are treated in the same manner as described in paragraph (1-a), whereby 2.14 g of methyl (±)-threo-2-hydroxy-3-(2-nitro-5-chlorophenylthio)-3-(4-methoxyphenyl)propionate are obtained.

M.p. 141°–143° C.

(2) A mixture of 22.0 g of methyl (±)-threo-2-hydroxy-3-(2-nitro-5-chlorophenylthio)-3-(4-methoxyphenyl)propionate, 120 ml of 10% sodium hydroxide and 400 ml of methanol is stirred at room temperature for 5 hours. The reaction mixture is acidified with conc. hydrochloric acid, and crystalline precipitates are collected by filtration. The crystals are washed with water, dried and then recrystallized from methanol. 17.49 g of (±)-threo-2-hydroxy-3-(2-nitro-5-chlorophenylthio)-3-(4-methoxyphenyl)propionic acid are obtained as plates.

M.p. 179°–182° C.

(3) 350 mg of (±)-threo-2-hydroxy-3-(2-nitro-5-chlorophenylthio)-3-(4-methoxyphenyl)propionic acid are dissolved in a mixture of 5 ml of ethanol and 5 ml of acetic acid, and 40 mg of 10% palladium-charcoal are added thereto. The mixture is shaken at room temperature in hydrogen gas atmosphere for 6 hours under an atmospheric pressure. After the reaction is completed, insoluble materials are filtered off. The filtrate is evaporated under reduced pressure to remove solvent, and the residue is recrystallized from a mixture of dimethylformamide and ethanol. 269 mg of (±)-threo-2-hydroxy-3-(2-amino-5-chlorophenylthio)-3-(4-methoxyphenyl)propionic acid are obtained.

The physico-chemical propereties of this product are identical with those of the product obtained in Preparation 2-(2).

Preparation 6

(1) 8.04 g of (±)-threo-2-hydroxy-3-(2-nitro-5-chlorophenylthio)-3-(4-methoxyphenyl)propionic acid are dissolved in 110 ml of methanol, and 3.85 g of L-lysine hydrochloride are added thereto. 21 ml of 1N potassium hydroxide-methanol are added to the mixture under ice-cooling, and the mixture is allowed to stand at room temperature. Crystalline precipitates are collected by filtration (the mother liquor is hereinafter referred to as "mother liquor (I)"). The crystals (10.56 g) are recrystallized three times from a mixture of dimethylformamide and water (1:1) (the mother liquors are hereinafter referred to as "mother liquor (II)"). 4.29 g of (+)-threo-2-hydroxy-3-(2-nitro-5-chlorophenylthio)-3-(4-methoxyphenyl)propionic acid L-lysine salt are obtained.

M.p. 244°–246° C. (decomp.)

The product (4.29 g) obtained above is suspended in water, and the suspension is acidified with diluted hydrochloric acid and then extracted with chloroform. The extract is washed with water, dried and then evaporated under reduced pressure to remove solvent. The residue is recrystallized from isopropanol. 3.36 g of (+)-threo-2-hydroxy-3-(2-nitro-5-chlorophenylthio)-3-(4-methoxyphenyl)-propionic acid are obtained.

M.p. 93°–97° C.

$[\alpha]_D^{20} + 138.7°$ (C=0.623, chloroform)

Analysis calculated for $C_{16}H_{14}O_6NSCl \cdot C_3H_7OH$ C, 51.41; H, 4.99; N, 3.16; S, 7.22; Cl, 7.99 Found: C, 51.25; H, 4.81; N, 3.30; S, 7.21; Cl, 7.87

The mother liquors (I) and (II) obtained above are combined, and concentrated under reduced pressure. Crystalline precipitates are collected by filtration and recrystallized from a mixture of ethanol and water (1:1). 3.61 g of (−)-threo-2-hydroxy-3-(2-nitro-5-chlorophenylthio)-3-(4-methoxyphenyl)propionic acid·L-lysine salt are obtained.

M.p. 229°–231° C. (decomp.)

The salt (3.61 g) thus obtained is converted into its free acid by using diluted hydrochloric acid and then recrystallized from isopropanol. 2.80 g of (−)-threo-2-hydroxy-3-(2-nitro-5-chlorophenylthio)-3-(4-methoxyphenyl)propionic acid are obtained.

M.p. 92°–97° C.

$[\alpha]_D^{20} - 120.2°$ (C=0.323, chloroform)

Analysis calculated for $C_{16}H_{14}O_6NSCl \cdot C_3H_7OH$ C, 51.41; H, 4.99; N, 3.16; S, 7.22; Cl, 7.99 Found: C, 51.12; H, 4.64; N, 3.68; S, 7.63; Cl, 8.32

(2-a) 362 mg of (+)-threo-2-hydroxy-3-(2-nitro-5-chlorophenylthio)-3-(4-methoxyphenyl)propionic acid are treated in the same manner as described in Preparation 5-(3), and the crude product is recrystallized from methanol. 301 mg of (+)-threo-2-hydroxy-3-(2-amino-5-chlorophenylthio)-3-(4-methoxyphenyl)propionic acid are obtained.

The physico-chemical properties of this product are identical with those of the product obtained in Preparation 4-(1).

(2-b) 350 mg of (−)-threo-2-hydroxy-3-(2-nitro-5-chlorophenylthio)-3-(4-methoxyphenyl)propionic acid are treated in the same manner as described in Preparation 5-(3), and the crude product is recrystallized from methanol. 260 mg of (−)-threo-2-hydroxy-3-(2-amino-5-chlorophenylthio)-3-(4-methoxyphenyl)propionic acid are obtained.

The physico-chemical properties of this product are identical with those of the product obtained in Preparation 4-(1).

Preparation 7

1.87 g of (±)-cis-2-(4-methoxyphenyl)-3-hydroxy-8-chloro-2,3-dihydro-1,5-benzothiazepin-4(5H)-one are dissolved in 10 ml of pyridine, and 0.52 g of acetyl chloride is dropwise added thereto. The mixture is stirred at room temperature for one hour. After the reaction is completed, chloroform is added to the mixture, and said mixture is washed with 10% hydrochloric acid, dried and then evaporated under reduced pressure to remove solvent. The residue is recrystallized from chloroform, whereby 1.4 g of (±)-cis-2-(4-methoxyphenyl)-3-acetoxy-8-chloro-2,3-dihydro-1,5-benzothiazepin-4(5H)-one are obtained as colorless needles.

M.p. 220°–223° C.

Preparation 8

3 g of (+)-cis-2-(4-methoxyphenyl)-3-hydroxy-8-chloro-2,3-dihydro-1,5-benzothiazepin-4(5H)-one, 0.77 g of acetyl chloride and 20 ml of pyridine are treated in the same manner as described in Preparation 7. The crude product is recrystallized from a mixture of ether and n-hexane. 1.6 g of (+)-cis-2-(4-methoxyphenyl)-3-acetoxy-8-chloro-2,3-dihydro-1,5-benzothiazepin-4(5H)-one are thereby obtained as colorless needles.

M.p. 120°–122° C.

$[\alpha]_D^{20} +58.7°$ (C=1.0, methanol)

What we claim is:

1. A compound of the formula:

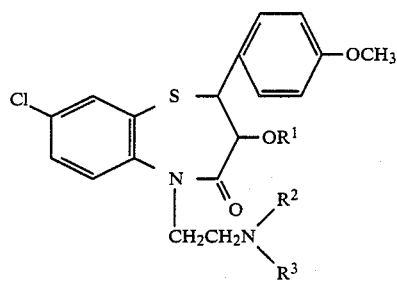

(I)

wherein $R^1$ is hydrogen, lower alkyl or a group of the formula: $R^4CO—$, each of $R^2$ and $R^3$ is lower alkyl and $R^4$ is lower alkyl, or a pharmaceutically acceptable acid addition salt thereof.

2. The compound claimed in claim 1, in which $R^1$ is hydrogen, methyl, acetyl, propionyl, butyryl or valeryl, and each of $R^2$ and $R^3$ is alkyl of one to 3 carbon atoms.

3. The compound claimed in claim 1, in which $R^1$ is hydrogen, methyl, acetyl or propionyl, and each of $R^2$ and $R^3$ is methyl or ethyl.

4. The compound claimed in claim 1, in which $R^1$ is a group of the formula: $R^4CO—$, wherein $R^4$ is lower alkyl.

5. The compound claimed in claim 3, in which $R^1$ is methyl, acetyl or propionyl, $R^2$ is methyl and $R^3$ is methyl or ethyl.

6. The compound claimed in claim 6, in which $R^1$ is acetyl or propionyl, and $R^2$ and $R^3$ are methyl.

7. The compound claimed in claim 6, in which $R^1$ is acetyl and $R^2$ and $R^3$ are methyl.

8. A cis isomer of the compound claimed in either one of claim 1, 3, 6 or 7.

9. A (+)-cis isomer of the compound claimed in either one of claim 1, 3, 6 or 7.

10. The compound of claim 7, which is (+)-cis-2-(4-methoxyphenyl)-3-acetoxy-5-[2-(dimethylamino)ethyl]-8-chloro-2,3-dihydro-1,5-benzothiazepin-4(5H)-one or a pharmaceutically acceptable acid addition salt thereof.

11. The compound of claim 7, which is (+)-cis-2-(4-methoxyphenyl)-3-acetoxy-5-[2-(N-methyl-N-ethylamino)ethyl]-8-chloro-2,3-dihydro-1,5-benzothiazepin-4(5H)-one or a pharmaceutically acceptable acid addition salt thereof.

12. The compound of claim 6, which is (+)-cis-2-(4-methoxyphenyl)-3-propionyloxy-5-[2-(dimethylamino)ethyl]-8-chloro-2,3-dihydro-1,5-benzothiazepin-4(5H)-one or a pharmaceutically acceptable acid addition salt thereof.

13. A compound of the formula:

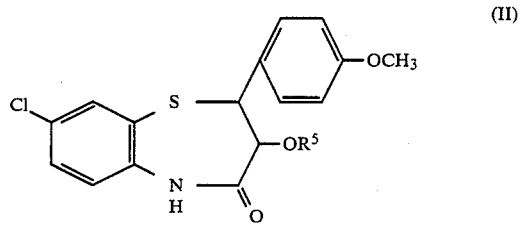

(II)

wherein $R^5$ is hydrogen or a group of the formula: $R^4CO—$ and $R^4$ is lower alkyl, or a salt thereof.

14. A pharmaceutical composition possessing hypotensive, cerebral vasodilating or coronary vasodilating activity which comprises a therapeutically effective amount of a compound according to claims 1, 3, 6, 7, or 10 and a pharmaceutically acceptable carrier therefor.

15. A method of producing a hypotensive effect on a warm-blooded animal comprising administering to said warm-blooded animal an effective amount of the compound claimed in claims 1, 3, 6, 7, or 10 or.

16. A method of producing a cerebral vasodilating effect on a warm-blooded animal comprising administering to said warm-blooded animal an effective amount of the compound claimed in claims 1, 3, 6, 7, or 10.

17. A method of producing a coronary vasodilating effect on a warm-blooded animal comprising administering to said warm-blooded animal an effective amount of the compound claimed in claims 1, 3, 6, 7, or 10.

18. The compound according to claim 6, wherein $R^1$ is acetyl or methyl and $R^2$ and $R^3$ are each methyl.

19. The compound according to claim 18 which is (+)-cis-2-(4-methoxyphenyl)-3-methoxy-5-[2-(dimethylamino)ethyl]-8-chloro-2,3-dihydro-1,5-benzothiazepin-4(5H)-one or a pharmaceutically acceptable acid addition salt thereof.

20. A compound of the formula:

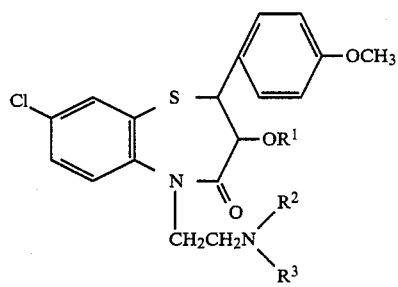

wherein $R^2$ and $R^3$ are each lower alkyl, or a salt thereof.

* * * * *

UNITED STATES PATENT AND TRADEMARK OFFICE
CERTIFICATE OF CORRECTION

PATENT NO. : 4,567,175
DATED : January 28, 1986
INVENTOR(S) : Mikio Takeda, et al.

It is certified that error appears in the above-identified patent and that said Letters Patent are hereby corrected as shown below:

In Claim 6, Column 25, Line 48 of the Patent, change "6" to --5--.

In Claim 8, Column 25, Line 53 of the Patent, change "6 or 7" to --6, 7 or 18--.

In Claim 9, Column 25, Line 55 of the Patent, change "6 or 7" to --6, 7 or 18--.

In Claim 14, Column 26, Lines 25-26 of the Patent, change "or 10" to --10 or 18--.

In Claim 15, Column 26, Line 30 of the Patent, change "or 10 or" to --10 or 18--.

In Claim 16, Column 26, Line 34 of the Patent, change "or 10" to --10 or 18--.

In Claim 17, Column 26, Line 38 of the Patent, change "or 10" to --10 or 18--.

UNITED STATES PATENT AND TRADEMARK OFFICE
CERTIFICATE OF CORRECTION

PATENT NO. : 4,567,175  
DATED : January 28, 1986  
INVENTOR(S) : Mikio Takeda, et al.

Page 2 of 2

It is certified that error appears in the above-identified patent and that said Letters Patent is hereby corrected as shown below:

In Claim 18, Column 26, Line 39 of the Patent, change "6" to --5--.

Signed and Sealed this

Nineteenth Day of August 1986

[SEAL]

Attest:

Attesting Officer

DONALD J. QUIGG

Commissioner of Patents and Trademarks